United States Patent [19]

Homeier

[11] 3,948,999

[45] Apr. 6, 1976

[54] HYDROFORMYLATION OF AN UNSATURATED COMPOUND
[75] Inventor: Edwin H. Homeier, Maywood, Ill.
[73] Assignee: Universal Oil Products Company, Des Plaines, Ill.
[22] Filed: Aug. 13, 1973
[21] Appl. No.: 387,995

[52] U.S. Cl. .................... 260/604 HF; 260/632 HF
[51] Int. Cl.² ......................................... C07C 47/20
[58] Field of Search ............... 260/604 HF, 632 HF

[56] References Cited
UNITED STATES PATENTS
3,725,305   4/1973   Wilkinson..................... 260/604 HF OTHER PUBLICATIONS
Broadbent et al., Journal of Organic Chem., Vol. 28, 1963, pp. 2347–2350.

*Primary Examiner*—James O. Thomas, Jr.
*Assistant Examiner*—R. H. Liles
*Attorney, Agent, or Firm*—James R. Hoatson, Jr.; Raymond H. Nelson; William H. Page, II

[57] ABSTRACT

An unsaturated compound is subjected to a hydroformylation reaction which comprises reacting said unsaturated compound with carbon monoxide and hydrogen in the presence of a catalyst containing a rhenium complex.

9 Claims, No Drawings

HYDROFORMYLATION OF AN UNSATURATED COMPOUND

This invention relates to a process for the preparation of hydroformylation products. More specifically, this invention relates to a process for the selective preparation of linear hydroformylation products which comprises hydroformylating an unsaturated compound with carbon monoxide and hydrogen in the presence of a catalyst comprising a rhenium complex.

Processes directed to the production of reaction mixtures comprising substantial amounts of aldehydes and alcohols by the hydroformylation of unsaturated compounds with carbon monoxide and hydrogen in the presence of certain catalysts are well-known in the art. The aldehydes and alcohols produced generally correspond to the compounds obtained by the addition of a carbonyl or carbinol group to an olefinically unsaturated carbon atom in the starting material with simultaneous saturation of the olefinic bond. The process is known as hydroformylation and involves a reaction which may be shown by the general generic formula:

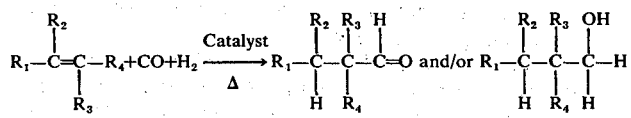

where $R_1$, $R_2$, $R_3$, $R_4$ may be chosen from a group comprising an organic, halide or hydrogen radical.

It has been shown in the prior art that a hydroformylation catalyst may comprise a complex catalyst consisting essentially of a metal having an atomic number of from about 75 to 78 inclusively in complex with carbon monoxide and/or a trialkyl phosphine. It has also been shown that dicobaltoctacarbonyl has also generally been used as a catalyst for hydroformylation of unsaturated compounds.

A serious disadvantage of hydroformylation processes has been the necessity of proceeding in two steps when alcohols are the desired products. Another disadvantage inherent in the hydroformylation is a relative inability to direct reactions involved to the production of predominantly terminal alcohols when the unsaturated compound contains more than two carbon atoms, particularly when the charge to the process comprises primarily internal unsaturated compounds. The desire for linear hydroformylation products possessing the carbonyl or carbinol function at a terminal position has increased due to the use of synthetic detergents inasmuch as some of the nonlinear or nonterminal detergents are nonbiodegradable in nature gives rise to a buildup of unwarranted foam or spume which do not disperse but remain on the surface of standing water, such as ponds, streams, rivers, lakes, etc. The presence of this unwanted foam or spume is of particular importance inasmuch as it remains in sources of water which are utilized for drinking purposes, swimming, etc., in towns or cities. Many communities have reported that it is likely that their tap water is heavily laced with suds due to the contamination of septic tanks. A method to eliminate the unwanted foam or spume is to create a synthetic detergent which is linear and possesses terminal bonding for the carbonyl or carbinol moiety. The biodegradable detergents must contain long chained alkyl substituents which are straight chained in configuration or which may contain a minimum amount of branching, said branching preferably comprising no more than methyl radicals. It can be seen from a discussion of the prior art hereinbefore set forth that it is desirable for the manufacturer for aldehydes and alcohols to prepare a hydroformylation product which is selectively linear and selectively terminal in respect to the bonding of the carbonyl or carbinol moiety.

In contradistinction to the prior art, it has now been shown that the utilization of a catalyst comprising a rhenium complex in the hydroformylation process will give an increase in selective linearity of the resultant aldehydes and alcohols. It is to be understood that the term "linear selectivity" as used in the specification and the appended claims means the mathematical relationship of the percent of normal aldehydes plus the percent of normal alcohols divided by the percent total aldehyde and alcohol formation. A greater market will be more readily available to the manufacturer of the alcohols and aldehydes by utilizing the process of this invention. The utilization of the present invention will also alleviate the demand for normal aldehydes and alcohols which may be converted to synthetic biodegradable detergents. Another advantage of the present invention is that it will allow the manufacturer to reduce his cost of production and thereby eventually reduce the cost of products made from the linear alcohols and the linear aldehydes to the consumer.

The desired products to the process of the present invention, namely alcohols and aldehydes, are used in the chemical industry in many ways. For example, linear alcohols and linear aldehydes are useful as intermediates in the preparation of desired biodegradable detergents, said alcohols being used as alkylating agents which after reaction with benzene may be sulfonated by any method known in the art. Alcohols are also utilized in the synthesizing of other organic derivatives, as solvents, as an extraction medium, in dyes, synthetic drugs, synthetic rubber, detergents, cleaning solutions, surface coatings, cosmetics, pharmaceuticals, in the preparation of esters, as a solvent for resin in coatings, as a plasticizer, dyeing assistant, hydraulic fluids, detergent formulations, dehydrating agents, or the use of aldehydes as exemplified by the utility as perfumery, or in the synthesis of primary alcohols.

It is therefore an object of this invention to provide a process for preparing aldehydes and alcohols.

A further object of this invention is to provide a process for selective preparation of linear hydroformylated products, namely linear alcohols and linear aldehydes, in a manner which is more economically expedient utilizing certain catalytic compositions of matter.

In one aspect an embodiment of this invention resides in a process for the selective preparation of linear hydroformylation products which comprises hydroformylating an unsaturated compound with carbon monoxide and hydrogen in the presence of a catalyst containing a rhenium complex at reaction conditions and recovering the resultant hydroformylated products.

A specific embodiment of this invention is found in a process for the hydroformylation of an unsaturated compound which comprises hydroformylating heptene-3 with carbon monoxide and hydrogen in the presence of a catalyst derived from perrhenate ions at a temperature in the range of from about 175°C to about 225°C and a pressure in the range of from about 100 atmospheres of carbon monoxide to about 110 atmospheres of carbon monoxide and a pressure of 100 atmospheres of hydrogen to about 110 atmospheres of hydrogen, and recovering the resultant aldehyde and alcohol, namely octanal and octanol.

A second specific embodiment of this invention is found in a process for the hydroformylation of an unsaturated compound which comprises hydroformylating decene-5 with carbon monoxide and hydrogen in the presence of a catalyst derived from perrhenate ions at a temperature of 200°C and a pressure of 100 atmospheres of carbon monoxide and 100 atmospheres of hydrogen, and recovering the resultant aldehyde and alcohol, namely undecanal and undecanol.

Other objects and embodiments will be found in the following further detailed description of the present invention.

As hereinbefore set forth, the present invention is concerned with a process for select preparation of linear alcohols and linear aldehydes, said process being effected by hydroformylating an unsaturated compound with carbon monoxide and hydrogen in the presence of a catalyst containing a rhenium complex. The reaction is effected under conditions which include a temperature in the range of from about 60°C to about 300°C. In addition, another reaction condition involves pressure, said pressure ranging from atmospheric up to 500 atmospheres or more. When superatmospheric pressures are employed said pressure is afforded by the introduction of gaseous carbon monoxide and hydrogen to the reaction zone, or if so desired any inert gas such as nitrogen, argon, helium, etc. In a preferred embodiment of the present invention the carbon monoxide and hydrogen are usually present in a 50/50% mixture of the two gases.

Examples of an unsaturated compound which may be hydroformylated by treatment with carbon monoxide and hydrogen in the presence of the catalytic composition of matter will include, in particular, butene-1, butene-2, pentene-1, pentene-2, hexene-1, hexene-2, hexene-3, heptene-1, heptene-2, heptene-3, octene-1, octene-2, octene-3, octene-4, nonene-1, nonene-2, nonene-3, nonene-4, decene-1, decene-2, decene-3, decene-4, decene-5, undecene-1, undecene-2, undecene-3, undecene-4, undecene-5, dodecene-1, dodecene-2, dodecene-3, dodecene-4, dodecene-5, dodecene-6, tridecene-1, tridecene-2, tridecene-3, tridecene-4, tridecene-5, tridecene-6, tetradecene-1, tetradecene-2, tetradecene-3, tetradecene-4, tetradecene-5, tetradecene-6, tetradecene-7, etc., while examples of suitable branch-chained unsaturated compounds which may be utilized as the starting material of the process of the present invention would include, in particular, 2-methylbutene-1, 3-methylbutene-1, 2-methylpentene-1, 2-methylpentene-2, 3-methylpentene-1, 4-methylpentene-1, 4-methylpentene-2, 2-methylhexene-1, 2-methylhexene-3, 2-methylheptene-1, etc., or mixtures of linear internal olefins such as internal olefins possessing carbon numbers of between 11 and 14 or 15 and 18, etc.

It is understood that the aforementioned unsaturated compounds are only representative of the class of compounds which may be employed as the starting material of the process of the present invention and that the present invention is not necessarily limited thereto.

The catalytic composition of matter of the process of the present invention contains a rhenium complex. The catalytic composition of matter may be formed in situ from a rhenium-containing compound in a homogeneous solution which may be either aqueous or organic in nature. The medium of the solution (commonly known as the solvent) may comprise an aqueous acid such as hydrochloric acid, sulfuric acid, nitric acid, bromic acid, etc., or an aqueous base such as sodium hydroxide, ammonium hydroxide, calcium hydroxide, etc., or a neutral aqueous solution. Alternatively, the solvent may comprise a non-aqueous medium such as a paraffinic hydrocarbon, an alcohol, chlorocarbon or other inert organic solvent. The rhenium catalyst may be formed in situ from a catalyst precursor such as rhenic acid, rhenic pentachloride, rhenium carbonyl, rhenium trichloride, rhenium tribromide, rhenium oxychloride, rhenium oxybromide, rhenium sesquioxide, rhenium trioxide, rhenium heptoxide, rhenium disulfide, rhenium heptasulfide, potassium thioperrhenate, potassium perrhenate, sodium perrhenate, cesium perrhenate, rubidium perrhenate, magnesium perrhenate, strontium perrhenate, etc.

Another preferred embodiment within the scope of the hereinbefore disclosed invention provides that the rhenium complex catalyst may be preformed in an appropriate medium such as n-pentane, n-hexane, methanol, chloroform, etc., by heating an appropriate catalyst precursor with carbon monoxide andd hydrogen. It is also contemplated within the scope of this invention that other Group VIIB complexes may be utilized in place of the rhenium complex, such as manganese or technetium complexes, although not necessarily with equivalent results.

It is understood that the aforementioned mediums and catalyst precursors in the formation of the rhenium complex are only representative of the class of compounds which may be employed, and that the present invention is not necessarily limited thereto.

In a preferred embodiment of the above disclosed invention, it is also contemplated that the hydroformylation may be effected in an organic media as exemplified by n-pentane, n-hexane, n-heptane, n-octane, n-nonane, isooctane(2,2,4-trimethylpentane), cyclohexane, methylcyclohexane, benzene, toluene, etc.

The process of this invention may be effected in any suitable manner and may comprise either a batch or continuous type operation. For example, when a batch-type operation is employed, the reactants comprising the unsaturated compound, carbon monoxide and hydrogen are placed in an appropriate apparatus capable of withstanding superatmospheric pressures along with a catalyst containing a rhenium complex. The autoclave is sealed, heated to a desired operating temperature and maintained thereat for a predetermined residence time. At the end of this time, which may comprise from about 0.5 up to about 20 hours or more in duration, the heating is discontinued, the autoclave is allowed to return to room temperature and vented, thereby allowing the autoclave to return to ambient pressure. The reaction mixture is then recovered, separated from the rhenium complex catalyst and subjected to conventional means of purification and separation, said means including washing, drying, extraction, evaporation, fractional distillation, etc., whereby the desired aldehyde or alcohol is recovered.

It is also contemplated within the scope of this invention that the hydroformylation process for obtaining the desired aldehydes and alcohols with increased linear selectivity may be effected in a continuous manner of operation. When such a type of operation is employed, the reactants comprising the unsaturated compounds are continuously charged to the hydroformylation reaction zone including the catalyst containing a rhenium complex, said hydroformylation zone being maintained at the proper operating conditions of temperature and hydrogen and carbon monoxide pressure by heat and the admission of the requisite quantities of carbon monoxide and hydrogen as required for effecting the hydroformylation reaction. After completion of the desired residence time, the reactor effluent is continuously withdrawn and subjected to conventional means of separation whereby the desired alcohols or aldehydes are recovered while any carbon monoxide, hydrogen, unreacted unsaturated compounds or rhenium complex catalyst are recycled to the hydroformylation reaction zone to form a portion of the continuous process. The rhenium metal may also be recovered from the hydroformylation reaction mixture by various methods known to the art and regenerated to form fresh catalyst.

Examples of aldehydes and alcohols which may be prepared according to the process of this invention, being lineary in nature, and containing the aldehydic or alcoholic moieties on a terminal carbon atom will include butanol, pentanol, hexanol, heptanol, octanol, nonanol, decanol, undecanol, dodecanol, tridecanol, tetradecanol, pentanal, hexanal, heptanal, octanal, nonanal, decanal, undecanal, dodecanal, tridecanal, tetradecanal, etc.

The following examples are given to illustrate the process of the present invention which, however, are not intended to limit the generally broad scope of the present invention in strict accordance therewith.

EXAMPLE I

In this example a solution containing perrhenate complexes was prepared by the addition of rhenic acid to hydrochloric acid in such a proportion so as to add the equivalent of 1.65 grams of rhenium for every 500 ml of acidic medium added.

To an 850 milliliter glass-lined rotating stainless steel autoclave was added 196.0 mmols of heptene-3 and the solution containing the perrhenate complex as described above in an amount equivalent to 1.3 mmol of rhenium, said rotating autoclave being equipped with heating and pressure attainment devices. The rotating autoclave was sealed, pressurized by the entry of 100 atmospheres of carbon monoxide and 100 atmospheres of hydrogen, heated to a temperature of 200°C and maintained thereat for a period of time comprising 67 hours. At the end of the 67 hour period of time, the heating was terminated thereby allowing the rotating autoclave to return to room temperature; the carbon monoxide and hydrogen were carefully vented thereby allowing said autoclave to return to ambient pressure. At this point, the product was removed from the glass-lined rotating autoclave and analyzed by means of gas-liquid chromatography instrumentation, said analysis disclosed that the product contained 59% total alcohol and 14% total aldehyde. The linear selectivity, herein defined as the mathematical relationship of the total percentage of normal aldehydes plus the total percentage of normal alcohols divided by the total percentage of aldehydes plus alcohols, was found to be 38%. The linear aldehyde and alcohol which was found to have the aldehydic or alcoholic moiety on the terminal carbon atom was octanal and octanol respectively.

EXAMPLE II

This example was performed to show the decrease in the linear selectivity during hydroformylation as a result of the change in the composition of matter of the catalyst.

To an 850 milliliter glass-lined autoclave was added 143 mmols of heptene-3 and rhodium dichlorodicarbonyl equivalent to 0.16 mmol of rhodium, said rotating autoclave being equipped with heating and pressure attainment devices. The rotating autoclave was sealed, pressurized by the entry of 30 atmospheres of carbon monoxide and 30 atmospheres of hydrogen, heated to a temperature of 60°C, and maintained thereat for a period of time comprising 3 hours. At the end of the 3 hour period of time, the heating was terminated thereby allowing the rotating autoclave to return to room temperature; the carbon monoxide and hydrogen were carefully vented thereby allowing said autoclave to return to ambient pressure. At this point the product was removed from the glass-lined rotating autoclave and analyzed by means of gas-liquid chromatography instrumentation, said analysis disclosed the product to be 30% aldehyde and less than 1 percent alcohol. The linear selectivity was found to be 5%. The aldehyde possessing the aldehydic moiety on the terminal carbon atom was found to be octanal.

It can be seen from a comparison of Examples I and II that the linear selectivity decreased 33% out of a possible 38% by the exchange of the rhodium catalyst for the homogeneous solution containing the rhenium complex catalyst.

EXAMPLE III

To an 850 milliliter glass-lined rotating autoclave was added 142.0 mmols of decene-5 and the solution containing the perrhenate complex as described in Example I above in an amount equivalent to 1.9 mmol of rhenium, said autoclave being equipped with heating and pressure attainment devices. The rotating autoclave was sealed, pressurized by the entry of 100 atmospheres of carbon monoxide and 100 atmospheres of hydrogen, heated to a temperature of 200°C and maintained thereat for a period of time comprising 67 hours. At the end of the 67 hour period of time, the heating was terminated thereby allowing the rotating autoclave to return to room temperature; the carbon monoxide and hydrogen were carefully vented thereby allowing the said autoclave to return to ambient pressure. At this point, the product was removed from the glass-lined rotating autoclave and analyzed by means of gas-liquid chromatography instrumentation, said analysis disclosed the product contained 74% total alcohol and 1% total aldehyde. The linear selectivity of the final product was disclosed to be 37%. The linear aldehyde and alcohol which was found to have the aldehydic or alcoholic moiety on the terminal carbon atom was undecanal and undecanol respectively.

EXAMPLE IV

This example was performed to show the decrease in the linear selectivity during the hydroformylation when compared to Example III above as a result of the change in the composition of matter of the catalyst.

To an 850 milliliter glass-lined autoclave was added 143.0 mmols of decene-5 and dicobaltoctacarbonyl equivalent to 0.1 mmol of cobalt, said rotating autoclave being equipped with heating and pressure attainment devices. The rotating autoclave was sealed, pressurized by the entry of 50 atmospheres of carbon monoxide and 50 atmospheres of hydrogen, heated to a temperature of 120°C, and maintained thereat for a period of time comprising 8 hours. At the end of the 8 hour period of time, the heating was terminated thereby allowing the rotating autoclave to return to room temperature; the carbon monoxide and hydrogen were carefully vented thereby allowing said autoclave to return to ambient pressure. At this point the product was removed from the glass-lined rotating autoclave and analyzed by means of gas-liquid chromatography instrumentation, said analysis disclosed the product to be 73% aldehyde and 2% alcohol with a linear selectivity of 24%. The linear aldehyde and alcohol which was found to have the aldehydic or alcoholic moiety on the terminal carbon atom was undecanal and undecanol respectively.

It can be seen from a comparison of Examples III and IV that the linear selectivity decreased 13% out of a possible 37% by the exchange of the cobalt catalyst for the homogeneous solution containing the rhenium complex catalyst.

EXAMPLE V

To an 850 milliliter glass-lined rotating autoclave was added 142.0 mmols of decene-5 and the solution containing the perrhenate complex as hereinbefore described in Example I in an amount equivalent to 1.9 mmols of rhenium, said autoclave being equipped with heating and pressure attainment devices. The rotating autoclave was sealed, pressurized by the entry of 25 atmospheres of carbon monoxide and 100 atmospheres of hydrogen, heated to a temperature of 200°C, and maintained thereat for a period of time comprising 67 hours. At the end of the 67 hour period of time the heating was terminated thereby allowing the rotating autoclave to return to room temperature; the carbon monoxide and hydrogen were carefully vented thereby allowing said autoclave to return to ambient pressure. At this point the product was removed from the glass-lined rotating autoclave and analyzed by means of gas-liquid chromatography instrumentation, said analysis disclosed the product to be 17% total alcohol and 1% total aldehyde. The linear selectivity was disclosed to be 40%. The linear aldehyde and alcohol which was found to have the aldehydic or alcoholic moiety on the terminal carbon atom was undecanal and undecanol respectively.

EXAMPLE VI

This example was performed to show the decrease in the linear selectivity during the hydroformylation when compared to Example V as a result of the change in the composition of matter of the catalyst.

To an 850 milliliter glass-lined autoclave was added 143.0 mmols of decene-5 and dicobaltoctacarbonyl equivalent to 0.1 mmol of cobalt, said rotating autoclave being equipped with heating and pressure attainment devices. The rotating autoclave was sealed, pressurized by the entry of 50 atmospheres of carbon monoxide and 50 atmospheres of hydrogen, heated to a temperature of 120°C, and maintained thereat for a period of time comprising 8 hours. At the end of the 8 hour period of time the heating was terminated thereby allowing the rotating autoclave to return to room temperature; the carbon monoxide and hydrogen were carefully vented thereby allowing the said autoclave to return to ambient pressure. At this point, the product was removed from the glass-lined rotating autoclave and analyzed by means of gas-liquid chromatography instrumentation, said analysis disclosed the product to be 13% aldehyde and 7% alcohol with a linear selectivity of 33%. The linear aldehyde and alcohol which were found to have the aldehydic or alcoholic moiety on the terminal carbon atom was undecanal and undecanol respectively.

It can be seen from a comparison of Examples V and VI that the linear selectivity decreased 7% out of a possible 40% by the exchange of the cobalt catalyst for the homogeneous solution containing the rhenium complex catalyst.

EXAMPLE VII

In this example a solution containing a rhenium complex is prepared by the addition of solid rhenium carbonyl to n-pentane in such a proportion as to assure an adequate supply of the rhenium complex per volume of inert organic medium.

To an 850 milliliter glass-lined rotating autoclave is added the tetradecene-7 solution containing the rhenium complex catalyst as described in the preceding paragraph, said autoclave being equipped with a reaction media of n-pentane and heating and pressure attainment devices. The rotating autoclave is sealed, pressurized by the entry of 100 atmospheres of carbon monoxide and 100 atmospheres of hydrogen, heated to a temperature of 200°C and maintained thereat for a period of time comprising 20 hours. At the end of the 20 hour period of time the heating is terminated thereby allowing the rotating autoclave to return to room temperature; the carbon monoxide and hydrogen are carefully vented thereby allowing said autoclave to return to ambient pressure. At this point the product is removed from the glass-lined rotating autoclave and analyzed by means of gas-liquid chromatography instrumentation, said analysis disclosed a substantially greater percentage of linear selectivity of the aldehydes and alcohols than would normally have been expected if another catalyst known to the art would have been utilized.

EXAMPLE VIII

This example was performed to show that the rhenium complex catalyst can be preformed from the catalyst precursors.

An aqueous solution comprised of 2.5 grams of rhenium as perrhenate and 100 milliliters of hydrochloric acid was added to an 850 milliliter glass-lined rotating autoclave along with 100 milliliters of n-pentane. The rotating autoclave was sealed, pressurized by the entry of 100 atmospheres of carbon monoxide and 100 atmospheres of hydrogen, heated to a temperature of 200°C and maintained thereat for a period of time comprising 18 hours. At the end of the 18 hour period of time the heating was terminated thereby allowing the autoclave to return to room temperature; the carbon monoxide and hydrogen were carefully vented thereby allowing said autoclave to return to ambient pressure. The rhenium complex catalyst which had been dissolved in the n-pentane was removed and stored below room temperature. An analysis of a sample of the stored catalyst by evaporation of the n-pentane and subsequent examination by atomic absorption instrumentation disclosed that the catalyst contained about 0.1 mmol of rhenium per milliliter of n-pentane.

A 1 milliliter portion of the preformed catalyst solution was added to 142.0 mmols of decene-5 in an 850 milliliter glass-lined rotating autoclave, said autoclave being equipped with heating and pressure attainment devices. The rotating autoclave was sealed, pressurized by the entry of 100 atmospheres of carbon monoxide and 100 atmospheres of hydrogen, heated to 200°C and maintained thereat for a period of time comprising 18 hours. At the end of the 18 hour period of time the heating was terminated thereby allowing the rotating autoclave to return to room temperature; the carbon monoxide and hydrogen were carefully vented thereby allowing said autoclave to return to ambient pressure. At this point the product was removed from the glass-lined rotating autoclave and analyzed by means of gas-liquid chromatography instrumentation, said analysis disclosed the product to be 23% total alcohol and 6% total aldehyde. The linear selectivity was disclosed to be 32%. The linear aldehyde and alcohol which were found to have the aldehydic or alcoholic moiety on the terminal carbon atom were undecanal and undecanol respectively.

I claim as my invention:

1. A process for the selective preparation of linear aldehydes and alcohols which comprises hydroformylating an unsaturated compound with carbon monoxide and hydrogen in the presence of a catalyst containing rhenium complex at a temperature in the range of about 60°C. to about 300°C. and a pressure of from about one atmosphere to about 500 atmospheres and recovering the resultant aldehydes and alcohols.

2. The process of claim 1 further characterized in that the unsaturated compound is heptene-3.

3. The process of claim 1 further characterized in that the unsaturated compound is decene-5.

4. The process of claim 1 further characterized in that the unsaturated compound is tetradecene-7.

5. The process of claim 1 further characterized in that the rhenium complex is present in a homogeneous solution.

6. The process of claim 1 further characterized in that the rhenium catalyst precursor is present as a perrhenate.

7. The process of claim 1 further characterized in that the rhenium catalyst presursor is present as a rhenium carbonyl.

8. The process of claim 1 further characterized in that the hydroformylation is effected in an inert organic medium.

9. The process of claim 1 further characterized in that said complex is the addition product of rhenic acid and hydrochloric acid.

* * * * *